US00PP14738P2

(12) United States Plant Patent
Henning

(10) Patent No.: US PP14,738 P2
(45) Date of Patent: Apr. 27, 2004

(54) CHRYSANTHEMUM PLANT NAMED 'FOXY YOPATRICIA'

(50) Latin Name: *Chrysanthemum×morifolium*
Varietal Denomination: Foxy Yopatricia

(75) Inventor: Jill Henning, DeMotte, IN (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 10/396,527

(22) Filed: Mar. 25, 2003

(51) Int. Cl.[7] ..... A01H 5/00
(52) U.S. Cl. ..... Plt./287
(58) Field of Search ..... Plt./287

*Primary Examiner*—Bruce R. Campell
*Assistant Examiner*—Annette H. Para
(74) *Attorney, Agent, or Firm*—C. A. Whealy

(57) ABSTRACT

A distinct cultivar of Chrysanthemum plant named 'Foxy Yopatricia', characterized by its upright, outwardly spreading and mounded plant habit; freely branching habit; uniform and freely flowering habit; decorative-type inflorescences; red-colored ray florets; and natural season flowering in late September in the Northern Hemisphere.

1 Drawing Sheet

Botanical classification/cultivar designation: *Chrysanthemum×morifolium* cultivar Foxy Yopatricia.

BACKGROUND OF THE INVENTION

The present invention relates to a new and distinct cultivar of Chrysanthemum plant, botanically known as *Chrysanthemum×morifolium,* commercially known as a garden-type Chrysanthemum and hereinafter referred to by the name 'Foxy Yopatricia'.

The new Chrysanthemum is a naturally-occurring whole plant mutation of the Chrysanthemum cultivar Yopatricia, disclosed in U.S. Plant Pat. No. 11,907. The new Chrysanthemum was discovered and selected by the Inventor as a single flowering plant within a population of plants of the cultivar Yopatricia in a controlled environment in DeMotte, Ind. in September, 2000. The selection of this plant was based on its unique ray floret coloration.

Asexual reproduction of the new cultivar by terminal cuttings taken in a controlled environment in Gainesville, Fla. since January, 2001, has shown that the unique features of this new Chrysanthemum are stable and reproduced true to type in successive generations.

SUMMARY OF THE INVENTION

The cultivar Foxy Yopatricia has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Foxy Yopatricia'. These characteristics in combination distinguish 'Foxy Yopatricia' as a new and distinct cultivar:

1. Upright, somewhat outwardly spreading and mounded plant habit.
2. Freely branching habit; dense and full plants.
3. Uniform and freely flowering habit.
4. Decorative-type inflorescences.
5. Red-colored ray florets.

6. Natural season flowering in late September in the Northern Hemisphere.

Plants of the new Chrysanthemum are most similar to plants of the the cultivar Yopatricia. In side-by-side comparisons conducted in Alva, Fla., plants of the new Chrysanthemum differed from plants of the cultivar Yopatricia in the following characteristics:

1. Plants of the new Chrysanthemum were smaller than plants of the cultivar Yopatricia.
2. Plants of the new Chrysanthemum flowered about two days later than plants of the cultivar Yopatricia.

Plants of the new Chrysanthemum can also be compared to plants of the Chrysanthemum cultivar Bravo, disclosed in U.S. Plant Pat. No. 6,888. In side-by-side comparisons conducted in Alva, Fla., plants of the new Chrysanthemum differed from plants of the cultivar Bravo in the following characteristics:

1. Plants of the new Chrysanthemum were shorter and more mounded than plants of the cultivar Bravo.
2. Plants of the new Chrysanthemum flowered about ten days later than plants of the cultivar Bravo.
3. Plants of the new Chrysanthemum had smaller inflorescences than plants of the cultivar Bravo.
4. Ray floret color of plants of the new Chrysanthemum did not fade as readily as ray floret color of plants of the cultivar Bravo.

BRIEF DESCRIPTION OF THE PHOTOGRAPHS

The accompanying photographs illustrate the overall appearance of the new Chrysanthemum. These photographs show the colors as true as it is reasonably possible to obtain in colored reproductions of this type. Colors in the photographs may differ slightly from the color values cited in the detailed botanical description which accurately describe the colors of the new Chrysanthemum.

The photograph at the top of the sheet comprises a side perspective view of a typical flowering plant of 'Foxy Yopatricia'.

The photograph at the bottom of the sheet comprises a close-up view of typical inflorescences of the cultivar 'Foxy Yopatricia'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in an outdoor nursery in Salinas, Calif., under natural season conditions and practices which approximate those generally used in commercial garden-type Chrysanthemum production. One cutting was planted in a 15.25-cm container in late May, 2002. Plants were not pinched, that is, the terminal apex was not removed to enhance branching. During the production of the plants, day temperatures averaged 20° C. and night averaged 13° C. Measurements and numerical values represent averages for typical flowering plants.

Botanical classification: *Chrysanthemum×morifolium* cultivar Foxy Yopatricia.

Commercial classification: Decorative-type garden Chrysanthemum.

Parentage: Naturally-occurring whole plant mutation of the *Chrysanthemum×morifolium* cultivar Yopatricia, disclosed in U.S. Plant Pat. No. 11,907.

Propagation:

*Type.*—Terminal tip cuttings.

*Time to initiate roots.*—About four days at 21° C.

*Time to produce a rooted cutting.*—About ten to twelve days at 21° C.

*Root description.*—Fine, fibrous; white in color.

*Rooting habit.*—Freely branching.

Plant description:

*Appearance.*—Perennial herbaceous decorative-type garden Chrysanthemum. Inverted triangle with rounded crown. Stems initially upright, then somewhat outwardly spreading giving a uniformly mounded appearance to the plant. Freely branching with lateral branches forming at every node.

*Plant height.*—About 21 cm.

*Plant diameter.*—About 27 cm.

*Lateral branches.*—Length: About 19 cm. Diameter: About 4 mm. Internode length: About 1.75 cm. Aspect: Upright and outwardly spreading. Texture: Pubescent. Color: 146A overlain with 187A.

*Foliage description.*—Leaf arrangement: Alternate. Length: About 3.1 cm. Width: About 2.7 cm. Apex: Cuspidate to mucronate. Base: Attenuate with truncate tendencies. Margin: Palmately lobed, sinuses mostly divergent. Texture, upper surface: Slightly pubescent. Texture, lower surface: Pubescent; veins prominent. Color: Developing and fully expanded foliage, upper surface: 147A. Developing and fully expanded foliage, lower surface: Darker than 147B. Venation, upper surface: 147A to 147B. Venation, lower surface: 147B. Petiole length: About 8 mm. Petiole diameter: About 2.5 mm. Petiole color, upper surface: 147B to 147C. Petiole color, lower surface: 147B.

Inflorescence description:

*Appearance.*—Decorative-type inflorescence form with elongated oblong-shaped ray florets. Inflorescences borne on terminals above foliage, arising from leaf axils. Disk and ray florets developing acropetally on a capitulum. About eight inflorescences per lateral.

*Flowering response.*—Under natural season conditions, plants flower in late September in the Northern Hemisphere.

*Inflorescence bud (before showing color).*—Height: About 5 mm. Diameter: About 7 mm. Shape: Oblate. Color (lower surface of phyllaries): 147A.

*Inflorescence size.*—Diameter: About 3.9 cm. Depth (height): About 1.5 cm. Disc diameter: No disc florets observed. Receptacle diameter: About 5 mm.

*Ray florets.*—Shape: Elongated oblong. Length: About 1.9 cm. Corolla tube length: About 2 mm. Width: About 5 mm. Apex: Emarginate. Margin: Entire. Texture: Smooth, glabrous; satiny. Surface: Concave to slightly convex. Orientation: Initially upright, then perpendicular to vertical. Number of ray florets per inflorescence: About 165 in numerous whorls. Color: When opening, upper surface: Close to 12A faintly overlain with 46A. When opening, lower surface: Close to 12D underlain with 53A to 59A. Opened inflorescence, upper surface: Close to 12A overlain with 46A; becoming closer to 12A overlain with 46A to 53A with development. Opened inflorescence, lower surface: Close to 12D underlain with 59A.

*Disc florets.*—None observed.

*Peduncle.*—Strength: Strong. Aspect: About 45° from vertical. Length: First peduncle: About 6.2 cm. Fourth peduncle: About 9.1 cm. Seventh peduncle: About 10.8 cm. Diameter: About 2 mm. Texture: Pubescent. Color: 146A overlain with 187A.

*Phyllaries.*—Quantity per inflorescence: About 35. Length: About 5 mm. Width: About 1.5 mm. Shape: Ligulate. Apex: Acute. Base: Truncate. Margin: Entire. Texture, upper surface: Smooth, waxy. Texture, lower surface: Pubescent. Color, upper surface: 146A. Color, lower surface: 147A.

*Reproductive organs.*—Androecium: None observed. Gynoecium: Present on ray florets.

*Seed/fruit.*—Seed and fruit production has not been observed.

Disease/pest resistance: Plants of the new Chrysanthemum have not been shown to be resistant to pathogens and pests common to Chrysanthemums.

Garden performance: Plants of the new Chrysanthemum have been observed to be tolerant to rain, wind and temperatures ranging from 0 to more than 37° C.

It is claimed:

1. A new and distinct cultivar of Chrysanthemum plant named 'Foxy Yopatricia', as illustrated and described.

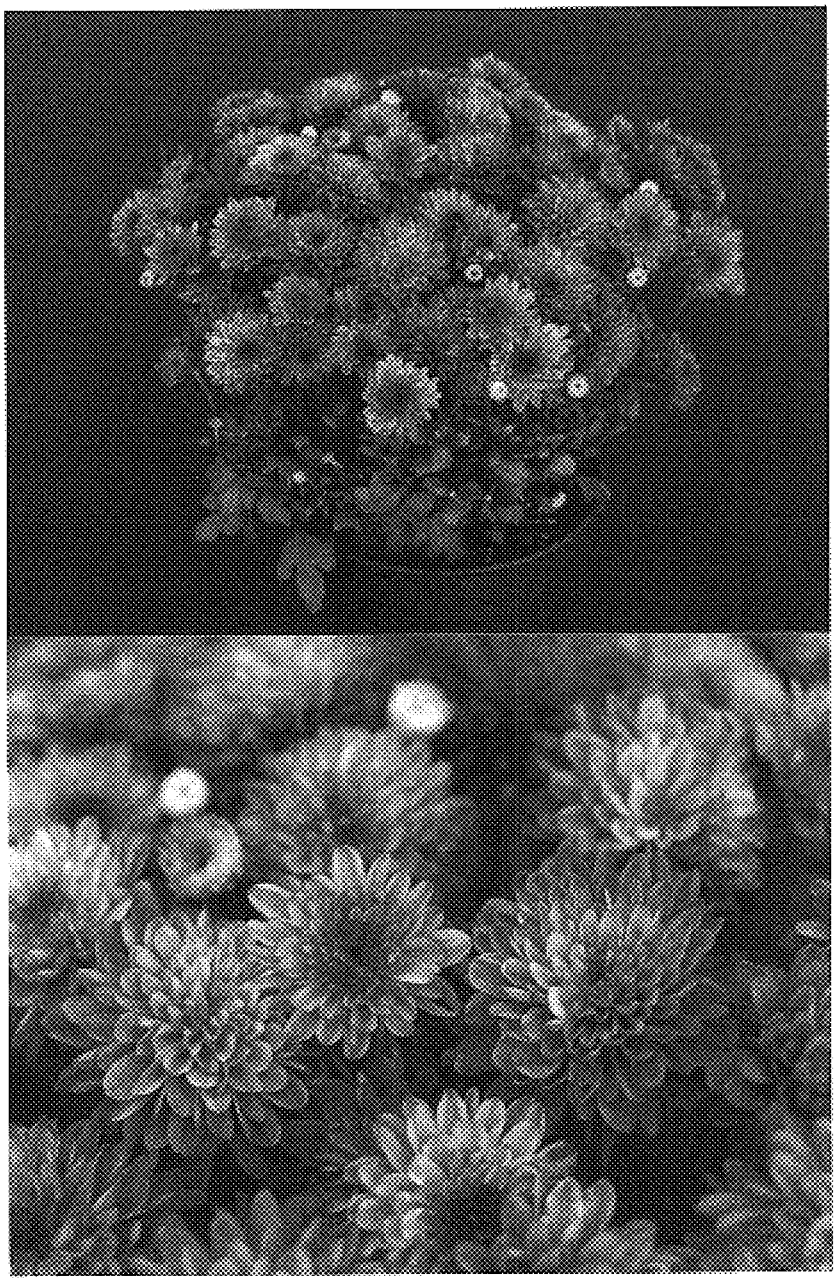

* * * * *